United States Patent [19]

Van Woensel et al.

[11] Patent Number: 5,925,359

[45] Date of Patent: Jul. 20, 1999

[54] EUROPEAN VACCINE STRAINS OF THE PORCINE REPRODUCTIVE AND RESPIRATORY SYNDROME VIRUS

[75] Inventors: Petrus Alphonsus Maria Van Woensel; Jean Guillaume Joseph Demaret, both of Boxmeer, Netherlands

[73] Assignee: Akzo Nobel, N.V., Arnhem, Netherlands

[21] Appl. No.: 08/947,696

[22] Filed: Oct. 9, 1997

[30] Foreign Application Priority Data

Oct. 9, 1996 [EP] European Pat. Off. .............. 96202804

[51] Int. Cl.$^6$ .......................... A61K 39/12; A61K 39/21; C12N 7/00; C07K 1/00

[52] U.S. Cl. .................................... 424/204.1; 424/218.1; 424/209.1; 424/815; 435/235.1; 435/236; 435/237; 435/238; 530/350

[58] Field of Search .............................. 424/204.1, 218.1, 424/209.1, 815; 435/235.1, 236, 237, 238, 239; 530/350

[56] References Cited

U.S. PATENT DOCUMENTS

| | | | |
|---|---|---|---|
| 5,510,258 | 4/1996 | Sanderson et al. | 435/237 |
| 5,587,164 | 12/1996 | Sanderson et al. | 424/218.1 |
| 5,695,766 | 12/1997 | Paul et al. | 424/204.1 |
| 5,698,203 | 12/1997 | Visser et al. | 424/218.1 |

FOREIGN PATENT DOCUMENTS

| | | |
|---|---|---|
| 0676467 | 10/1995 | European Pat. Off. . |
| WO 93/07898 | 4/1993 | WIPO . |
| WO 94/18311 | 8/1994 | WIPO . |

*Primary Examiner*—Lynette F. Smith
*Attorney, Agent, or Firm*—William M. Blackstone; Mary E. Gormley

[57] ABSTRACT

The present invention is concerned with European strains of the Porcine Reproductive Respiratory Syndrome (PRRS) virus, having as a unique feature that they are non-infectious to macrophages, and to methods for the production of such strains. The invention also provides vaccines for the protection of pigs against PRRS, based on these strains, as well as methods for the production of such vaccines.

19 Claims, No Drawings

EUROPEAN VACCINE STRAINS OF THE PORCINE REPRODUCTIVE AND RESPIRATORY SYNDROME VIRUS

FIELD OF THE INVENTION

The present invention is concerned with a live attenuated strain of a European serotype of the Porcine Reproductive and Respiratory Syndrome Virus (PRRSV), methods for the production of such strains, vaccines based thereon and methods for the production of such vaccines.

BACKGROUND OF THE INVENTION

In 1987, an until then unknown disease in pigs was detected in North America, from where it later spread to Canada (Hill, H.; In: Proceedings of the Mystery Swine Disease Committee meeting, Oct. 6, 1990, Denver, Colo., Livestock Conservation Institute, Madison Wis, U.S.A., Keffaber et al; Am. Assoc. Swine Pract. Newsletter 1: 1–9 (1989)). The disease, which was characterized by the fact that it induced both abortion and respiratory disease, was first called Mystery Swine Disease (MSD). Nowadays, in America and Canada, the disease is also known as Swine Infertility and Respiratory Syndrome (SIRS).

Since 1990, the disease has been found in Europe, where it first caused outbreaks in Germany, followed by outbreaks in the Netherlands and Belgium, and the disease is now spreading through Europe. In Europe, the disease is commonly known as Porcine Reproductive Respiratory Syndrome (PRRS), and as Porcine Epidemic Abortion and Respiratory Syndrome (PEARS). Currently the disease is world-wide referred to as PRRS.

The pathology is not restricted to abortion and respiratory disease. Other symptoms associated with the disease are: off feed, anorexia, and bluish discolorations of the extremities, especially the ears.

The pathogenic effects of the disease with respect to both abortion and respiratory disease have extensively been described in the comprehensive review by Christianson et al. (Swine Health and Production 2: 10–28 (1994)).

The causative agent of the disease is now known to be a small enveloped RNA virus belonging to the group of Arteriviridae. Observations made by Wensvoort et al. (J. Vet. Diagn. Invest 4; 134–138 (1992) and by Murtaugh et al. (Arch. Virol. 140: 1451–1460 (1995) made it unequivocally clear that two fully different (sero)types of the virus exist: the American and the European (sero)type.

The European type of this virus has been described by Wensvoort et al. (The Vet. Quarterly; 13:121–130 (1991)). A strain of this European type, called the "Lelystad Virus" (LV) has been deposited with the Institut Pasteur, Paris, France under no. I-1102, in connection with PCT WO 92/21375 by the Central Veterinary Institute, Lelystad, The Netherlands. Another European strain has been described in EPA no. 91.202.646.5, and was deposited with the Collection Nationale de Cultures de Micro-organismes (CNCM) of the Institut Pasteur at Paris France under no. I-1140. This European strain has recently been described by Conzelmann et al. (Virology 193: 329–339 (1993)).

The American type of the virus has been described by Benfield et al. (J. Vet. Diagn. Invest. 4: 127–133 (1992)). A strain of the American type has been deposited with the ATCC under no VR-2332, and is mentioned in PCT WO 93/03760 and European Patent Application 0.529.584. An attenuated strain of the American serotype has been described in European Patent Application 0.529.584. This strain is directly derived from the deposited American VR-2332 strain. Therefore, animals vaccinated with this strain will not obtain an efficient protection against infection with European strains. This made it necessary to develop a live attenuated strain of the European serotype to be used as a basis for vaccines against European serotypes.

In European Patent Application No. EP 0.676.467 live attenuated strains of the European serotype are disclosed for the first time. Examples of attenuated strains of the European serotype are the virus strains PRRS C and PRRS D, as deposited with the Collection Nationale de Cultures de Micro-organismes (CNCM) of the Institut Pasteur at Paris, France, under the Accession number I-1387 (Strain D) and number I-1388 (Strain C).

These strains are effective as a basis for live attenuated vaccines against PRRSV. Nevertheless they still have a certain level of virulence left. Therefore, alternatively attenuated PRRSV strains and methods for the preparation of such viruses are desirable.

It is an object of the present invention to provide live attenuated PRRS-virus strains of a European serotype having the desired feature of alternative attenuation characteristics compared to the existing attenuated PRRS virus strains. It is another object of the present invention to provide methods for the preparation of such live attenuated PRRS virus strains.

These objectives are met by the present invention which provides live attenuated PRRS viruses of a European serotype that have the unique feature that they are not infectious to macrophages. It is shown in the Examples that such strains show a more attenuated character in pigs, than the parent strains that still are infectious to macrophages.

The wording "non-infectious to macrophages" has to be understood as follows: a dose of $<10^4$ Tissue Culture Infectious Doses $(TCID)_{50}$ according to the present invention does not give a visible CPE on a macrophage culture even at 7 days after infection. A typical macrophage-infectious PRRSV field strain would give a full CPE with infectious particle doses from 1 $TCID_{50}$ and up.

Viruses of the European serotype are characterized in that they give a higher serum titre in an Immunoperoxidase Monolayer Assay with a panel of antisera against the European PRRS virus LV (CDI-NL-2.91; as deposited with the Institut Pasteur under I-1102) compared to a reaction with a panel of antisera against the American PRRS virus SIRSV (ATCC VR-2332).

It is another feature of the invention that it provides methods for the preparation of live attenuated PRRS strains according to the invention. Currently, all European PRRSV strains are obtained from macrophages of infected animals, and then if possible kept on MA 104 cells or clones thereof for propagation. The methods according to the present invention relate to the adaptation of MA 104-grown PRRS virus to non-MA 104 cells. These non-MA 104 cells may, for example be cells with a limited life span, or established immortalized cell lines. In general, the non-MA 104 cells will be mammalian cells. Mammalian non-MA 104 cells are, for example, general purpose cell lines such as BHK cell lines, CRFK cell lines and Madin Darby Bovine Kidney cell lines or, for example porcine cells such as Swine testicle cells or Swine kidney cells, or they may be non-MA 104 primate cells such as VERO cells. Adapting PRRSV to cells other than the natural host cell comprises standard methods that can be performed as follows: a specific PRRS virus isolate is grown on a culture containing porcine cells or other susceptible cells of non-porcine origin, at which the virus can be multiplied, such as MA 104 cells. After growth, the PRRSV is harvested by collecting the cell culture fluids and/or cells followed by passage of the cell culture fluids and/or cells onto another cell type for adaptation. Strains that have first been adapted to one non-MA 104 cell line can additionally be adapted to another non-MA 104 cell line for further attenuation. If desired, this adaptation process can be repeated on still other non-MA 104 cells. Adaptation to growth at different temperatures may also be part of the attenuation process. After passage to non-MA 104 cells, the non-macrophage-infectious character can be obtained after a small number of passages. A number of 5 passages, usually the number of passages necessary to obtain a master seed virus, often suffices to obtain non-macrophage-infectious viruses according to the invention.

In a preferred form, the method uses non-MA 104 primate cells as the cells for the adaptation. It is clear that after adaptation to non-MA 104 primate cells any further adaptation can be done on any other suitable cells.

In a more preferred form, the method uses Vero cells as the non-MA 104 primate cells for the adaptation.

Checking for the non-macrophage-infectious character of the so obtained live attenuated strains can easily be done by testing the absence of growth of the so obtained strains in vitro on macrophages. Standard techniques for both the preparation of macrophage cultures and propagation of macrophage-infectious virus are known in the art, and have, for example, been described in WO 93/07898. A simple test system based on macrophages isolated and grown under standard conditions will do as a test system to discriminate live attenuated PRRS strains according to the invention from other live attenuated PRRS viruses that still retain their macrophage-infectious character. One possible test system is described in Example 2.

The attenuated character of PRRSV strains according to the present invention can be illustrated departing from two strains: I-1140, a pathogenic PRRSV strain isolated in 1991 in the Netherlands, and I-1387, a low pathogenic PRRSV field strain (both strains deposited with the Collection Nationale de Cultures de Micro-organisms (CNCM) of the Institut Pasteur at Paris France under their respective number). These parent strains are infectious for macrophages. Of these parent strains, attenuated non-macrophage-infectious strains according to the invention were made as described in Example 1. The macrophage-infectious character was determined as described in Example 2.

The following strains were available for tests:

1. I-1140 88$^{th}$ passage on MA 104 cells
2. I-1140 61$^{st}$ passage on Vero cells
3. I-1387 20$^{th}$ passage on MA 104 cells
4. I-1387 49$^{th}$ passage on Vero cells The following shows the test results checking for the infection-characteristics of these strains:

TABLE 1

Comparison of strains according to the invention and high passage numbers of the parent strains

| Strain | Macrophage | Cell-line Vero | MA104 |
| --- | --- | --- | --- |
| 1 | +++ | --- | +++ |
| 2 | --- | +++ | +++ |

TABLE 1-continued

Comparison of strains according to the invention and high passage numbers of the parent strains

| Strain | Macrophage | Cell-line Vero | MA104 |
| --- | --- | --- | --- |
| 3 | +++ | --- | +++ |
| 4 | --- | +++ | +++ |

Also very suitable as parent strains for attenuation according to the present invention are PRRS viruses that are already attenuated in another (i.e. not relating to macrophage infectivity) aspect. Such viruses have been described in European Patent Application No. EP 0.676.467, mentioned above. These virus strains belong to a European serotype and they are reactive with monoclonal antibody A27 as produced by hybridoma A27 deposited with the Collection Nationale de Cultures de Micro-organisms (CNCM) of the Institut Pasteur at Paris France under No. I 1401, but not with monoclonal antibody A35 as produced by hybridoma A35 deposited with the Institut Pasteur at Paris France under No. I 1402. If such viruses are made non-infectious to macrophages according to methods of the present invention, they are even more safe since then their attenuated character relies on two or more different aspects, one of which is the non-macrophage-infectious character. Therefore, in a more preferred embodiment of the present invention, the live attenuated PRRSV according to the invention has the additional characteristics of being reactive with monoclonal antibody A27 as produced by hybridoma A27 deposited with the Collection Nationale de Cultures de Micro-organisms (CNCM) of the Institut Pasteur at Paris France under No. I 1401, but not with monoclonal antibody A35 as produced by hybridoma A35 deposited with the Institut Pasteur at Paris France under No. I 1402.

Since the non-macrophage-infective strain according to the present invention derived from the I-1387 strain is so highly attenuated after passage over Vero cells, this live attenuated strain is extremely safe when administered to animals (see Example 2 and further). Therefore, in another more preferred embodiment of the present invention, the live attenuated PRRSV is of the strain that is deposited by AKZO Nobel NV at the Collection Nationale de Cultures de Microorganisms of the Institut Pasteur, 25 Rue du Docteur Roux, 75724 Paris Cedex 15 under Accession Number I-1758. This strain was given the Identification Reference "PRRSV strain DV" and thus will also be referred to as strain DV in this Specification.

The live attenuated viruses according to the present invention are, as a result of their inability to infect macrophages, a very suitable basis for vaccines for the following reason: These strains are not infectious to the macrophage. The macrophage is the primary target cell of wild-type PRRSV and one of the key cells of the immune system. Nevertheless, they still have retained their ability to trigger the immune system. Therefore, contrary to vaccines based on known live attenuated strains of the European serotype as described in European Patent Application No. EP 0.676.467, vaccines comprising the live attenuated viruses according to the present invention trigger the immune system without at the same time impairing it.

Thus, vaccines based on the strains of the present invention provide safety of a different kind than vaccines based on the known attenuated strains.

Therefore, in still another embodiment, the present invention provides vaccines for the protection of pigs against PRRSV infection, that are based on the live non-macrophage-infectious attenuated PRRS strains described above.

Due to the safety of the non-macrophage-infectious viruses, vaccines based on these viruses may typically contain $10^3$–$10^{10}$ live virus particles.

Vaccines according to the present invention may comprise a pharmaceutically acceptable carrier. One possible carrier is a physiological salt solution. Another pharmaceutically acceptable carrier is for instance the tissue culture fluid used for sustaining the cell growth, in which the viruses are released from the infected cells.

An adjuvant and if desired one or more emulsifiers such as Tween and Span may also be incorporated in the live attenuated vaccine according to the invention. Suitable adjuvants are for example vitamin E acetate solubilisate, aluminium hydroxide, -phosphate or -oxide, (mineral) oil emulsions such as Bayol and Marcol52, and saponins. Incorporation of the antigens in Iscoms is also a possible way of adjuvation.

The vaccine according to the invention is produced preferably in a freeze-dried form. It is advantageous to add a stabilizer to live attenuated viruses, particularly if a dry composition of live viruses is prepared by lyophilisation. Suitable stabilizers are, for example, SPGA (Bovamik et al., J. Bacteriology 59, 509, 1950), carbohydrates (such as sorbitol, mannitol, trehalose, starch, sucrose, dextran or glucose), proteins (such as albumin or casein), or degradation products thereof, and buffers (such as alkali metal phosphates). If desired, one or more compounds with adjuvant activity as described above can also be added.

A vaccine according to the invention may be administered by intramuscular or subcutaneous injection or via intranasal, intratracheal, oral, cutane, percutane/intradermal or intracutane administration. A very convenient way of administration is intradermal or intramuscular administration. Therefore, in a preferred embodiment, the vaccine according to the invention comprises a carrier that is suitable for intradermal or intramuscular application. A physiological salt solution is, for example a simple and suitable carrier for intradermal or intramuscular application.

The vaccine according to the invention can be administered to pigs depending on the vaccination history of the sows at 1, 3, 6 or 10 weeks of age, to sows before mating and/or up to 6 weeks before farrowing (booster vaccination), or to boars each half a year (boosters).

In a preferred form, the vaccine of the present invention comprises, next to live attenuated PRRS virus, another unrelated (i.e. non-PRRSV) attenuated or inactivated pathogen or antigenic material from another pathogen. Such a pathogen may be a bacterium or a parasite, but may also be of viral origin. Usually, the unrelated pathogen or antigenic material thereof will be a porcine pathogen. A vaccine according to the invention that also comprises such an additional attenuated or inactivated pathogen or antigenic material from another pathogen has the advantage that it induces protection against several infections at the same time. Antigenic material is understood to be material that is capable of inducing an immunogenic response. Examples of antigenic material are proteins, polysaccharides and lipopolysaccharides.

In a more preferred form, the pathogen is selected from the group of Pseudorabies virus, Porcine influenza virus, Porcine parvovirus, Transmissible gastroenteritis, Rotavirus, *Escherchia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae*.

A vaccine according to the invention may be derived from any live attenuated PRRS virus isolate of a European serotype according to the present invention. The deposited PRRSV strain DV, developed by using methods according to the present invention has all the characteristics that make it a very suitable vaccine strain. Thus in a preferred form, the vaccine is derived from PRRSV strain DV, deposited at the Institut Pasteur under Accession Number I-1758.

In again still another embodiment, the present invention provides methods for the preparation of a live attenuated vaccine for combating PRRS. A convenient way of obtaining a vaccine based on live attenuated PRRSV according to the invention comprises admixing a suitable amount of virus according to the invention with a pharmaceutically acceptable carrier.

Additionally, other materials, such as the adjuvants, emulsifiers and stabilizers mentioned above, can be added to improve the performance and the stability of the vaccine.

EXAMPLE 1

Adaptation Experiments

Adaptation of PRRSV isolate I-1140 to Vero cells:

I-1140, a pathogenic PRRSV strain isolated in 1991 in the Netherlands (mentioned above and deposited with the Collection Nationale de Cultures de Micro-organismes (CNCM) of the Institut Pasteur at Paris France under this number), was first cultured on porcine lung macrophages, and then grown on MA 104 cells as follows:

Semi-confluent monolayers of MA 104 cells (70 cm$^2$) were inoculated with the PRRSV strain at 80% confluence with an MOI of 1. Inoculation was done by first removing the tissue culture medium, then 1 ml of PRRSV virus was added and left on the monolayer for at least 2 hours at 37° C. After this period new tissue culture medium was added and the cells were incubated further at 37° C. in humidified $CO_2$ (5% $CO_2$). When CPE was observed the supernatant was collected and the cells were freeze thawed 3×, centrifuged for 10 minutes at 2000 rpm and the supernatant collected. Both supernatants were then pooled and used to inoculated a fresh monolayer of the same cells. This process was then repeated until the virus was fully adapted to the cell line and titres comparable to macrophage cultures could be obtained on this cell line. During this process the identity of the virus was determined by Immune Fluorescence Assay (IFA) with both PRRSV specific polyclonal serum and PRRSV specific monoclonal antibodies.

The 5th passage of I-1140 on MA 104 cells was used to infect CV1 (Green African monkey kidney) cells by the following method:

CV1 cells were grown under standard cell growth conditions. At 70 to 80% confluence the medium was removed from the CV1 monolayer. Supernatant obtained at maximum CPE from an infected monolayer of MA 104 cells was first filtered through a 0.2 μm filter and then placed on the CV1 monolayer. After one day of incubation at 37° C. and 5% $CO_2$ the medium was replaced by new tissue culture medium. Cells were incubated further at 37° C. and 5% $CO_2$ for 7 days. During this period cells were daily examined microscopically. After 7 days the cells were freeze thawed 3×, the supernatants harvested by centrifugation and filtered through a 0.2 μm filter. The filtered material was then used to incubate a new monolayer of CV1 cells as described above. This process was done for 3 rounds, after the third round the harvested and filtered supernatants were checked for the presence of PRRSV by incubating the supernatants on MA 104 cells. The presence of PRRSV was shown by the presence of a PRRSV specific fluorescence using the PRRSV specific monoclonal antibody I-1401. (Monoclonal antibody I-1401 has been deposited with the Collection Nationale de Cultures de Micro-organismes (CNCM) of the Institut Pasteur at Paris France under this number). A PRRSV titre of 6.6 $TCID_{50}$/ml was found in the supernatants of the CV1 cells. Passage 13 of I-1140 on CV1 cells was brought on Vero cells by the method described above. This time after 3 rounds of blind passages PRRSV was detected in the supernatants of Vero cells. The virus was further adapted to Vero cells by performing 61 passages on Vero cells. For comparison, the $88^{th}$ passage of the parent strain I-1140 on MA 104 cells, and thus not adapted to non-MA 104 cells was used as a control in Table 1, where the macrophage-infectivity of the various strains was compared.

Adaptation of PRRSV isolate I-1387 to Vero cells

Isolate I-1387 was first cultured on porcine lung macrophages. The 5th passages of I-1387 was then placed on MA 104 cells by the method described above. Passage 38 of I-1387 on MA 104 cells was used to infect Vero cells according the method given above. PRRSV was detected in the supernatants of the Vero cells. This isolate was further adapted to Vero cells by performing 49 passages on these cells. This strain was used in the safety experiments and vaccination challenge experiments described in Examples 2 and 3. For comparison, the $20^{th}$ passage of the parent strain I-1387 on MA 104 cells, and thus not adapted to non-MA 104 cells was used as a control in Table 1, where the macrophage-infectivity of the various strains was compared.

EXAMPLE 2

Macrophage Infectivity Test System

In this test, the four virus strains mentioned in Table 1 (vide supra) were checked for macrophage-infectivity as follows:

Swine alveolar macrophages were obtained as follows: SPF-pigs were sacrificed, their lungs were removed and washed with 3000 ml PBS. The cells were collected by centrifugation and resuspended in MEM-medium (GIBCO)+10% FCS to a concentration of $0.3 \times 10^6$ cells/ml. Finally, cells were seeded on 96-well microculture plates with 225 µl cell suspension/well and the plates were stored four days in a $CO_2$-incubator. Just before titration, the microtiter plates were emptied and refilled with fresh medium. 25 µl samples comprising $10^4$ MA 104-infectious virus particles of the virus to be tested were brought onto the wells and 10-fold serial dilution's were made. Finally the plates were incubated in a $CO_2$-incubator for 7 days. No growth on macrophages as measured by CPE could be detected for the strains that were adapted to non-MA 104-cells, whereas the non-adapted control strains were infectious for macrophages as expected. Results are shown in Table 1 (vide supra).

EXAMPLE 3

Attenuation Tests

To test if the adaptation of the virus to these cells did induce any positive attenuation of the virulence, all virus strains were tested in pregnant sows by the following method:

Sows, negative for PRRS virus and PRRSV specific antibodies, were infected with one of the PRRSV strains given above at approximately 90 days of gestation. To measure the virulence of a given strain the number of aborted piglets and piglet that died within a week were determined. The following results were obtained:

TABLE 2

Attenuation results

| Strain | Dose ($TCID_{50}$) | Born dead | Dead after one week | Alive after one week | Dead (%) | Alive (%) |
| --- | --- | --- | --- | --- | --- | --- |
| 1140 | $10^5$ | 13 | 11 | 9 | 73 | 26 |
| 1140 61p Vero | $10^{7.5}$ | 15 | 5 | 11 | 65 | 35 |
| 1387 | $10^{7.5}$ | 16 | 8 | 34 | 50 | 50 |
| 1387 49p Vero | $10^{8.6}$ | 1 | 4 | 25 | 17 | 83 |

It can be concluded from the above-given Table 2, that the PRRSV-strains that lost their macrophage infectivity show favorable attenuated characteristics. For I-1140 significantly less dead piglets were found after infection of sows with the non-macrophage-infective strain. Given the fact that, compared to the parent I-1140 strain, a three hundred-fold increase in dose of I-1140 adapted to Vero was administered, a very substantial reduction in virulence was established. A similar effect is observed in the experiment where I-1387 is given to sows. A dose of $10^{7.5}$ $TCID_{50}$ still induced a significant number of dead piglets. However, with the non-macrophage-infective strain a remarkable reduction in virulence was observed; although given at an extreme high dose (a 10 fold increase with respect to the dose of $10^{7.5}$ $TCID_{50}$), a significantly lower number of piglets was found dead.

EXAMPLE 4

Safety Experiments

I) Safety of strain DV in piglets aged 5–6 weeks. Single dose and high dose

Three experiments involved vaccination of target animals; young piglets. The set-up of these experiments is summarized in Table 3. For the safety test, the animals were screened for possible clinical signs, attributable to the vaccination.

TABLE 3

| Exp. No. | Dose $TCID_{50}$ | ml | Application method* | Age (weeks) | Number | Observation period days |
| --- | --- | --- | --- | --- | --- | --- |
| 131 | $10^{6.9}$ | 2 | i.m. | 5 | 10 | 28 |
| 135 | $10^{5.5}$ | 2 | i.m. | 5 | 10 | 28 |
|  | $10^{5.5}$ | 0.2 | i.d. | 5 | 10 | 28 |
|  | $10^{4.8}$ | 2 | i.m. | 5 | 10 | 28 |
|  | $10^{4.5}$ | 0.2 | i.d. | 5 | 10 | 28 |
|  | $10^{3.5}$ | 2 | i.m. | 5 | 10 | 28 |
|  | $10^{3.8}$ | 0.2 | i.d. | 5 | 10 | 28 |
| 192 | $10^{6.6}$ | 2 | i.m. | 6 | 8 | 3–15 |
|  | $10^{6.4}$ | 0.2 | i.d. | 6 | 8 | 3–15 |

*i.m.: intramuscular
i.d.: intradermal

Results

In these experiments, after vaccination no clinical signs attributable to the vaccination were noticed.

Conclusion

Strains according to the invention are perfectly safe for the target animal: the young piglet.

II) Safety for pregnant sows

The pregnant sow is regarded as the most sensitive animal for safety studies, because infection with PRRS virus at approximately 90 days of gestation leads to a high percentage of abortions and mummifications (30–100%) and to a high percentage of death in the first week after birth of piglets born alive. In this safety test, each sow was inoculated at 94 days of gestation both intramuscularly and intradermally with a massive dose of $10^{8.3}$ TCID$_{50}$ per injection site.

The investigations involved the following items:
Local and systemic reactions in the sows
Antibody level in the sows at parturition to show the "take" of the vaccine
Reproductive performance of the sows
Virus re-isolations from serum samples of piglets taken on the day of birth Results The antibody level measured in an Immune Fluorescence Assay was >8 (log$_2$) in all sows indicating that the vaccination had taken. After vaccination no systemic reactions were observed during a period of 5 days of temperature monitoring and 14 days of clinical observations. Only in one sow on day 7 post-i.m.-vaccination a minor local reaction was observed. During one week after intradermal application local skin-reactions were seen: redness, heat, palpable spots and some lesions. These local skin reactions rapidly disappeared and were no longer visible in the $2^{nd}$ week.

The results of the reproductive performance are summarized in Table 4:

TABLE 4

| Sow No. | Number of piglets that died | |
|---|---|---|
| | Before or at birth | During one week after birth |
| 4611 | 0 out of 12 | 1 out of 12 |
| 4608* | 0 out of 15 | 2 out of 15 |
| 465 | 1 out of 11 | 1 out of 11 |

*The two piglets from sow 4608 placed with sow 465 survived.

The number of piglets that survived is considered at least a normal average number (>=10.08 according to the Handboek voor de Varkenshouderij ISBN 90-800999-3-7). It is fully with the reproductive performances found earlier in these same sows.

Conclusion

Although given in extremely high dose at the optimal time point in gestation for inducing abortion in this experiment no clinical signs of PRRS virus infections were observed.

EXAMPLE 5

Vaccination-Challenge Experiments

In two vaccination-challenge experiments the protective properties of vaccination with PRRS virus according to the present invention were investigated. In both experiments groups of ten PRRS antibody free piglets were vaccinated at an age of 5 to 6 weeks with vaccine strain DV PRRS virus with titres varying from $10^{3.5}$ to $10^{6.9}$ TCID$_{50}$ (see also Table 2; groups 131 and 135). In these experiments also safety and spreading aspects were investigated. Four weeks after vaccination these piglets were challenged intranasally with $10^5$ TCID$_{50}$ of a heterologous wild-type PRRS virus. After vaccination and challenge the serological response was monitored in the vaccinated animal as well as in sentinel animals placed in direct contact with the vaccinates and controls placed in the same building but physically separated (different pen).

The major criterion to judge the protective properties of the vaccine was the amount of re-isolated challenge strain virus from serum obtained at various times after challenge. Re-isolation was determined with two different parameters: the period during which the challenge virus could be re-isolated and the titre of the virus at the moment of re-isolation were determined.

Results

Serological response

The antibody titres as measured in IFA in log$_2$ units after vaccination and challenge are presented in Table 5 for vaccinates, sentinels and controls.

TABLE 5

| | | | | | | | | Average antibody titre days following | | | | |
|---|---|---|---|---|---|---|---|---|---|---|---|---|
| | Application | | | | Vaccination | | | | Challenge | | | |
| Exp. No. | method | Dose | N | 0 | 14 | 21 | $28^2$ | $0^2$ | 3 | 7 | 10 | 13/14 |
| | | | | Vaccinates | | | | | | | | |
| 131 | i.m. | $10^{6.9}$ | 9 | 0 | 6.9 | 10.0 | 11.6 | 11.6 | | | | 12.0 |
| 135 | i.m. | $10^{5.5}$ | 10 | 0 | | | 9.7 | 9.7 | 10.9 | 10.3 | 11.6 | 10.7 |
| | i.d. | $10^{5.5}$ | 10 | 0 | | | 9.5 | 9.5 | 10.9 | 10.9 | 10.9 | 11.1 |
| | i.m. | $10^{4.8}$ | 10 | 0 | | | 10.0 | 10.0 | 11.4 | 10.8 | 11.4 | 11.3 |
| | i.d. | $10^{4.5}$ | 10 | 0 | | | 9.1 | 9.1 | 10.6 | 10.7 | 11.5 | 10.4 |
| | i.m. | $10^{3.5}$ | 10 | 0 | | | 9.3 | 9.3 | 10.2 | 9.8 | 12.1 | 11.4 |
| | i.d. | $10^{3.8}$ | 10 | 0 | | | 9.2 | 9.2 | 10.2 | 10.0 | 10.8 | 10.6 |
| | | | | Sentinels | | | | | | | | |
| | Placed in group | | | | | | | | | | | |
| 131 | i.m. | $10^{6.9}$ | 4 | 0 | 0 | 2.5 | 4.5 | 4.5 | | | | 11.5 |
| 135 | i.m. | $10^{5.5}$ | 2 | 0 | | | 0 | 0 | 0 | 0 | 9.3 | 9.8 |
| | i.d. | $10^{5.5}$ | 2 | 0 | | | 0 | 0 | 0 | 0 | 11.3 | 10.3 |
| | i.m. | $10^{4.8}$ | 2 | 0 | | | 4.7 | 4.7 | 7.8 | 7.8 | 10.8 | 10.3 |
| | i.d. | $10^{4.5}$ | 2 | 0 | | | 0 | 0 | 0 | 0 | 9.8 | 8.3 |
| | i.m. | $10^{3.5}$ | 2 | 0 | | | 0 | 0 | 0 | 3.7 | 7.3 | 9.3 |
| | i.d. | $10^{3.8}$ | 2 | 0 | | | 0 | 0 | 0 | 0 | 7.3 | 9.3 |
| | | | | Controls | | | | | | | | |
| 131 | | | 5 | 0 | 0 | 0 | 0 | 0 | | | | 1.6 |
| 135 | | | 12 | 0 | | | $0.7^3$ | $0.7^3$ | 0 | 0 | 7.4 | 8.7 |

TABLE 5-continued

| | | | Average antibody titre days following | | | | | | | | |
|---|---|---|---|---|---|---|---|---|---|---|---|
| | Application | | | Vaccination | | | | Challenge | | | |
| Exp. No. | method | Dose | N | 0 | 14 | 21 | $28^2$ | $0^2$ | 3 | 7 | 10 | 13/14 |

[1]i.m. = intramuscular
i.d. = intradermal
[2]Day 28 after vaccination = Day 0 after challenge
[3]non-specific levels The highest antibody titres were found in experiment 131. This experiment showed that a clear antibody response is already detectable at two weeks after vaccination. In both experiments, titres in the vaccinated animals were much higher than in the controls, also after challenge. This was especially the case in experiment 131. The serological response measured in experiment 135 after intramuscular and intradermal application was comparable. Possibly the lowest titres observed and the slowest booster reaction was seen in the group vaccinated with a dose of $10^{3.5}$ TCID$_{50}$ but also with this lowest dose tested, significant titres were obtained. Sentinels: 2 out of 4 animals seroconverted in experiment 131 and 1 out of 12 in experiment 135. In both experiments no seroconversion was seen in the controls kept in the same area as the vaccinates but physically separated.

Re-isolation (challenge) virus

Average PRRSV titres ($\log_{10}$) found in serum (averaged for each group) are shown in Table 6 for vaccinates, sentinels and controls.

TABLE 6

| Exp. No. | Applicat. method | Dose TCID$_{50}$ | N | Average virus titre days after challenge | | | | | Av. duration virus excretion in days |
|---|---|---|---|---|---|---|---|---|---|
| | | | | 0 | 3 | 6/7 | 10 | 13 | |
| Vaccinates | | | | | | | | | |
| 131 | i.m. | $10^{6.9}$ | | 0 | 0 | 0 | 0 | 0 | 0 |
| 135 | i.m. | $10^{5.5}$ | | 0 | 0.3 | 0.9 | 1.0 | 0.3 | 3.5 |
| | i.d. | $10^{5.5}$ | | 0 | 0.3 | 0.4 | 0.8 | 0.2 | 2.4 |
| | i.m. | $10^{4.8}$ | | 0 | 0.3 | 0.4 | 0.2 | 0 | 1.7 |
| | i.d. | $10^{4.5}$ | | 0 | 0.2 | 0.3 | 0.5 | 0.3 | 1.5 |
| | i.m. | $10^{3.5}$ | | 0 | 0.4 | 1.6 | 1.0 | 0 | 3.7 |
| | i.d. | $10^{3.8}$ | | 0 | 0.2 | 1.1 | 1.0 | 0 | 2.7 |
| Sentinels | | | | | | | | | |
| Placed in | | | | | | | | | |
| 131 | i.m. | $10^{6.9}$ | 4 | 0 | 1.3 | 2.9 | 3.3 | 2.6 | >13 |
| 135 | i.m. | $10^{5.5}$ | 2 | 0 | 2.4 | 3.8 | 3.6 | 1.9 | 13 |
| | i.d. | $10^{5.5}$ | 2 | 0 | 3.1 | 3.6 | 3.1 | 3.1 | 13 |
| | i.m. | $10^{4.8}$ | 2 | 0.9 | 0.7 | 0 | 1.6 | 0 | 6.5 |
| | i.d. | $10^{4.5}$ | 2 | 0 | 2.1 | 3.9 | 3.6 | 1.1 | 11.5 |
| | i.m. | $10^{3.5}$ | 2 | 0 | 2.4 | 3.6 | 4.1 | 3.1 | 13 |
| | i.d. | $10^{3.8}$ | 2 | 0 | 2.1 | 3.6 | 3.6 | 2.4 | 13 |
| Controls | | | | | | | | | |
| 131 | | | 5 | 0 | 0 | 2.9 | 3.9 | 3.4 | >13 |
| | | | 12 | 0 | 2.6 | 4.0 | 3.7 | 1.5 | 11.5 |

[1]i.m. = intramuscular
i.d. = intradermal

In experiment 131 no challenge virus was re-isolated from the vaccinated animals. In experiment 135 a significant reduction in re-isolation rate and duration of re-isolation was found in all groups in comparison with the unvaccinated controls. The effects regarding reduction in the group vaccinated intramuscularly with a dose of $10^{3.5}$ TCID$_{50}$ was slightly lower than in the other groups.

Only 2 out of 4 sentinels in experiment 131 seroconverted after vaccination, in experiment 135 only 1 out of 12 animals. In one other sentinel animal of the same group (i.m. $10^{4.5}$) PRRS virus was isolated at the time of challenge which was probably vaccine virus.

Conclusion

A clear antibody response is already detectable at two weeks after vaccination, and it mounts to high titres. The serological response after intramuscular and intradermal application is comparable. Even with a dose of $10^{3.5}$ TCID$_{50}$ significant titres are obtained. No re-isolation or a significantly reduced re-isolation rate and duration of re-isolation was found in all groups in comparison with the unvaccinated controls. The virus spreads to direct controls only at a very low rate. With this rate of spreading the vaccine virus will become extinct within a few rounds of replication further demonstrating the attenuated character of strains according to the invention.

We claim:

1. A live attenuated Porcine Reproductive and Respiratory Syndrome Virus (PRRSV) of a European serotype, which is not infectious to macrophages.

2. The live attenuated PRRSV according to claim 1, which is reactive with monoclonal antibody A27 as produced by hybridoma A27 deposited with the Collection Nationale de Cultures de Micro-organisms (CNCM) of the Institut Pasteur at Paris France under No. I-1401, but not with monoclonal antibody A35 as produced by hybridoma A35 deposited with the CNCM of the Institut Pasteur at Paris France under No. I-1402.

3. The live attenuated PRRSV according to claim 2, which is of the strain as deposited at the Institut Pasteur under Accession Number I-1758.

4. A method for the preparation of the live attenuated PRRSV according to claim 1, comprising adapting an MA 104-grown PRRSV of a European serotype to non-MA 104 mammalian cells.

5. The method according to claim 4, wherein non-MA104 primate cells are used as the non-MA104 mammalian cells.

6. The method according to claim 5, wherein Vero cells are used as the non-MA104 primate cells.

7. A vaccine for the protection of pigs against PRRSV infection, comprising the live attenuated PRRSV according to claim 1 and a pharmaceutically acceptable carrier.

8. The vaccine according to claim 7, which further comprises one or more non-PRRSV attenuated or inactivated pathogens or antigenic material thereof.

9. The vaccine according to claim 8, wherein said non-PRRSV pathogens are selected from Pseudorabies virus, Porcine influenza virus, Porcine parvovirus, Transmissible gastroenteritis virus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae*.

10. The vaccine according to claim 7, which comprises a carrier that is suitable for intradermal or intramuscular application.

11. The vaccine according to claim 7, which is in freeze-dried form.

12. A method for the preparation of a live attenuated vaccine for combating PRRS, comprising admixing a live attenuated PRRSV according to claim 1 with a pharmaceutically acceptable carrier.

13. The method according to claim 12, wherein the live attenuated PRRSV deposited at the Institut Pasteur under Accession Number I-1758 is used for admixing.

14. A vaccine for the protection of pigs against PRRSV infection, comprising the PRRSV according to claim 2 and a pharmaceutically acceptable carrier.

15. A vaccine for the protection of pigs against PRRSV infection, comprising the PRRSV according to claim 3 and a pharmaceutically acceptable carrier.

16. The vaccine according to claim 14, which further comprises one or more non-PRRSV attenuated or inactivated pathogens or antigenic material thereof.

17. The vaccine according to claim 16, wherein said non-PRRSV pathogens are selected from Pseudorabies virus, Porcine influenza virus, Porcine parvovirus, Transmissible gastroenteritis virus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae*.

18. The vaccine according to claim 15, which further comprises one or more non-PRRSV attenuated or inactivated pathogens or antigenic material thereof.

19. The vaccine according to claim 18, wherein said non-PRRSV pathogens are selected from Pseudorabies virus, Porcine influenza virus, Porcine parvovirus, Transmissible gastroenteritis virus, *Escherichia coli, Erysipelo rhusiopathiae, Bordetella bronchiseptica, Salmonella cholerasuis, Haemophilus parasuis, Pasteurella multocida, Streptococcus suis, Mycoplasma hyopneumoniae* and *Actinobacillus pleuropneumoniae*.

* * * * *